United States Patent [19]
Stave et al.

[11] Patent Number: 5,994,145
[45] Date of Patent: *Nov. 30, 1999

[54] REAGENTS, METHODS AND KITS FOR DETECTING TRICHLOROETHYLENE AND PERCHLOROETHYLENE

[75] Inventors: James W. Stave, Elkton, Md.; Cynthia A. Kozakiewicz, New Castle; Dale V. Onisk, Bear, both of Del.; Robert T. Hudak, Landenberg, Pa.

[73] Assignees: Strategic Diagnostics Inc., Newark, Del.; EM Industries, Inc., Hawthorne, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/652,643

[22] Filed: May 31, 1996

[51] Int. Cl.$^6$ .......................... G01N 33/00; G01N 33/566
[52] U.S. Cl. .......................... 436/139; 436/142; 436/145; 436/501; 436/536
[58] Field of Search .................................. 436/139, 142, 436/536, 145, 501

[56] References Cited

U.S. PATENT DOCUMENTS 5,145,790  9/1992  Mattingly et al. .
5,273,909  12/1993  Piasio .

FOREIGN PATENT DOCUMENTS 9317030  9/1993  WIPO .
WO 94/12536  6/1994  WIPO .

OTHER PUBLICATIONS

Kearney et al., "A New Mouse Myeloma Cell Line That Has Lost Immunoglobulin Expression But Permits The Construction of Antibody–Secreting Hybrid Cell Lines," *J. Immunology*, vol. 123, pp. 1548–1550 (Oct. 1979).

Hudak et al., Abstract of "Validation of An Immunoassay Field Screen for Trichloroethylene (TCE)," paper presented by Strategic Diagnostics, Inc. at International Symposium on Field Screening Methods for Hazardous Wastes and Toxic Chemicals, Feb. 22–24, 1995, Las Vegas, NV.

*Primary Examiner*—Anthony C. Caputa
*Assistant Examiner*—Mark Navarro
*Attorney, Agent, or Firm*—Jones & Askew, LLP

[57] ABSTRACT

Reagents, immunoassay methods, and kits for detecting the presence or amount of trichloroethylene or perchloroethylene in a sample. Reagents include antibodies, immunogens for preparing antibodies, and assay conjugates. The immunogens elicit high affinity antibodies to trichloroethylene. The antibodies have minimal crossreactivity to other halogenated and aromatic hydrocarbons. The assay conjugates provide for sufficient binding of the antibody to the conjugate with maximum inhibition of that binding by free trichloroethylene and perchloroethylene in the sample. The reagents are useful in immunoassays to detect trichloroethylene and perchloroethylene, especially in environmental samples. Kits contain antibodies specific for trichloroethylene and perchloroethylene and assay conjugates.

4 Claims, 1 Drawing Sheet

REAGENTS, METHODS AND KITS FOR DETECTING TRICHLOROETHYLENE AND PERCHLOROETHYLENE

FIELD OF THE INVENTION

This relates to the field of immunology and more specifically relates to immunoassay methods, antibodies, and other reagents for the detection of trichloroethylene and perchloroethylene.

BACKGROUND OF THE INVENTION

Environmental contamination is a severe problem endangering the lives of many plants and animals, including humans. Many attempts are being made to reduce contamination by either preventing escape of the contaminants into the environment, containing the contaminants, or treating the contaminants in some way to make them less harmful. However, the first step in contaminant elimination or reduction is the identification of the contaminant followed by a determination of the quantity of contamination at the contaminated site. As the contaminated site is treated, such as by contaminant removal, degradation or encapsulation, the site is monitored to determine the effectiveness of the clean-up procedure.

The current approach of collecting soil and water samples and sending them to a laboratory for chemical analysis is time-consuming, inefficient, costly, may result in inaccurate measurements, and can pose health and safety risks to workers and the community. Ideally, the degree of contamination remaining in a contaminated site during and after the clean-up procedure should be monitored by personnel at the site. For example, during a remediation effort involving large, expensive earth moving equipment, it is important to know whether all of the contaminated soil has been removed from a site before equipment and personnel are moved to the next job site. Immediate results regarding the extent of remaining contamination allow these decisions to be made in the most cost effective manner. To be effective in the field, contaminant monitoring methods must be simple, portable, rapid, unambiguous, able to withstand harsh environmental conditions, and should provide results that can be visualized at the test site, preferably in the absence of instrumentation.

A major component of the costs associated with a hazardous site characterization can be attributed to analytical testing. Gas chromatography (GC) and gas chromatography/mass spectroscopy (GC/MS) are common analytical methods utilized to evaluate environmental pollutants. Although highly sensitive, these methods require sophisticated equipment that are not easily adapted for use in the field. Portable gas chromatograph/mass spectrometers (GC/MS) for sample analysis in the field have been developed. However, the costs of production, maintenance, and operation of such instruments by highly trained technicians are understandably high.

Halogenated Hydrocarbons

Halogenated hydrocarbons have been identified as common pollutants in the United States. Halogenated hydrocarbons have been and still are widely used in many industries as cleaning solvents, refrigerants, fumigants, and starting materials for the syntheses of other chemicals. This class of contaminants includes volatile halogenated hydrocarbons, such as trichloroethylene, a general solvent and degreaser and the most prevalent halogenated hydrocarbon contaminant, and perchloroethylene (dry cleaning fluid). Because of the extensive use and stability of halogenated hydrocarbons, hundreds of contaminated groundwater and landfill sites exist in the United States.

Trichloroethylene (TCE) is a volatile compound, routinely used as a solvent in various industrial applications throughout the world. Because of its prevalent use, frequent releases of this compound from accidental spills, leaking storage containers and improper disposal practices have led to environmental contamination. Due to its potential teratogenic, mutagenic and carcinogenic properties coupled with a partition coefficient that suggests its ability to migrate quickly through soil, federal regulations have been enacted to limit trichloroethylene levels in the environment.

To determine if trichloroethylene contamination exists, an accurate and reliable site characterization must be performed. The extent of the contamination is determined by making borings at regular intervals across the entire site and taking samples from each boring every two to five feet until the water table is encountered. Trichloroethylene levels in these samples are used to project the extent of the contaminant plume. Because of the volatility associated with trichloroethylene, special sample collection, handling and storage techniques must be employed to minimize contaminant loss to evaporation and assure accuracy from the analysis. When dealing with volatile compounds, such as trichloroethylene, the most accurate and reliable results are usually obtained from on-site testing or 24 hour turn-around analyses.

Immunoassays

Various approaches have been described for carrying out immunoassays (e.g. P. Tijssen, PRACTICE AND THEORY OF ENZYME IMMUNOASSAYS, Elsevier, Amsterdam, 1985), which rely on the binding of analyte by an analyte receptor or antibody to determine the concentrations of analyte in a sample. The most widely applied immunoassay method for detection of small molecules, such as those having a molecular weight less than 1000 daltons, is the heterogeneous, competitive immunoassay. In the heterogeneous, competition immunoassay a structurally similar derivative or analog of the analyte to be detected is chemically coupled to a substance to form an analyte-conjugate. The analyte-conjugate is employed as a reagent in the assay and competes with analyte in the sample for antibody binding sites. Either the antibody or the analyte-conjugate is labeled in such a way as to render them detectable, and the immunoassay method provides a physical means for separating bound and unbound label. A sample suspected of containing analyte, the analyte-conjugate, and the antibody are reacted together. Bound and unbound label are separated and either can be quantitated as a measure of analyte concentration in the sample.

Environmental Immunoassays

Immunoassay methods have been available for the detection of some environmental contaminants for several years. However, a crucial step in the development of an immunoassay is the availability or production of antibodies that bind to the analyte to be detected. Small molecules such as trichloroethylene ($ClCHCCl_2$) and perchloroethylene ($C_2Cl_4$) are too small to produce an appropriate immune response when injected into laboratory animals. Such molecules, commonly referred to as haptens, must first be coupled to a larger molecule, commonly referred to as a carrier molecule, to produce a conjugate that then may be used to produce antibodies. However, the ability to produce antibodies to hapten is not predictable. Furthermore, even if antibodies to the hapten are produced, they may not possess sufficient sensitivity and specificity for the analyte to be utilized in an immunoassay having the requisite performance characteristics.

Antibodies for use in an immunoassay for the detection of small aliphatic organic compounds including trichloroethylene and perchloroethylene are available as described in U.S. Pat. No. 5,273,909 to Roger Piasio. However, these antibodies react better with other organic compounds such as toluene and therefore lack specificity for trichloroethylene.

Little progress on the development of inexpensive, onsite monitoring methods, such as immunoassay methods, has been made. Therefore, there is an on-going need for development of antibodies and immunoassays specific for the detection of trichloroethylene and perchloroethylene, particularly assays that are highly sensitive and specific, and can be used for on-site detection of environmental contamination.

SUMMARY OF THE INVENTION

Reagents, immunoassay methods, and kits for the detection of the analytes trichloroethylene and perchloroethylene in a sample are provided. The reagents are immunogens, antibodies, and assay conjugates.

The immunogens are haptens structurally similar to trichloroethylene and perchloroethylene conjugated to a carrier through a linker group and a spacer group. Immunization of an animal with the immunogen results in the production of antibodies specific for trichloroethylene and perchloroethylene. The chemical formula of the immunogen is set forth below.

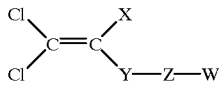

wherein X is Cl or H; Y is $CH_2$, NH, O or S; Z is 0–50 atoms arranged in a straight or branched chain or rings through saturated or unsaturated bonds; and W is an immunogenic carrier.

In a preferred immunogen, Y is $CH_2$ and Z is a straight chain containing oxygen and carbon atoms.

In a more preferred immunogen, X is Cl or H; Y is $CH_2$; Z is 1–9 oxygen and carbon atoms arranged in a straight chain through saturated bonds; and W is an immunogenic carrier.

Suitable immunogenic carriers include proteins, polypeptides, peptides, polysaccharides, carbohydrates, polymers, and solid phase substances.

The assay conjugate has a chemical formulation similar, but not identical, to that of the immunogen, namely:

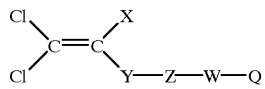

wherein X is Cl or H; Y is $CH_2$, NH, O or S; Z is 0–50 atoms arranged in a straight or branched chain or rings through saturated or unsaturated bonds; W is a chemical bond, protein, polysaccharide, peptide, polymer or other linking molecule; and Q is a detectable substance or solid phase. If W is a protein, it is a protein different from that utilized in the immunogen.

In a preferred assay conjugate, X is Cl; Y is $CH_2$; and Z is a straight chain containing nitrogen, oxygen and carbon atoms.

More preferably, X is Cl; Y is $CH_2$; Z is a straight chain containing nitrogen, oxygen and carbon atoms, including an aromatic ring; W is a protein, and Q is a detectable substance or solid phase.

Antibodies produced using the immunogens described above are useful in the development of immunoassays for the detection of trichloroethylene and perchloroethylene. Such antibodies have high affinity for trichloroethylene and perchloroethylene and react minimally with other halogenated and aromatic hydrocarbons.

Immunoassays employing the reagents described herein are capable of detecting low concentrations of trichloroethylene and perchloroethylene in contaminated samples and react minimally with other contaminants that may be present in the sample, thus providing for an accurate determination of trichloroethylene and perchloroethylene contamination.

It is therefore an object of the present invention to provide reagents, immunoassay methods, and kits for the detection of trichloroethylene and perchloroethylene in a sample, particularly an environmental sample.

It is a further object of the present invention to provide a highly sensitive immunoassay for trichloroethylene and perchloroethylene.

It is a further object of the present invention to provide an immunogen for the production of antibodies highly specific for trichloroethylene and perchloroethylene.

It is a further object of the present invention to provide high affinity antibodies for trichloroethylene and perchloroethylene that exhibit minimal crossreactivity with other halogenated and aromatic hydrocarbons.

It is a further object of the present invention to provide an assay conjugate for use in immunoassays for the detection of trichloroethylene and perchloroethylene.

These and other objects of the present invention will become apparent after reading the following detailed description of the disclosed embodiments and the appended claims.

DETAILED DESCRIPTION OF THE DISCLOSED EMBODIMENTS

Figure 1:
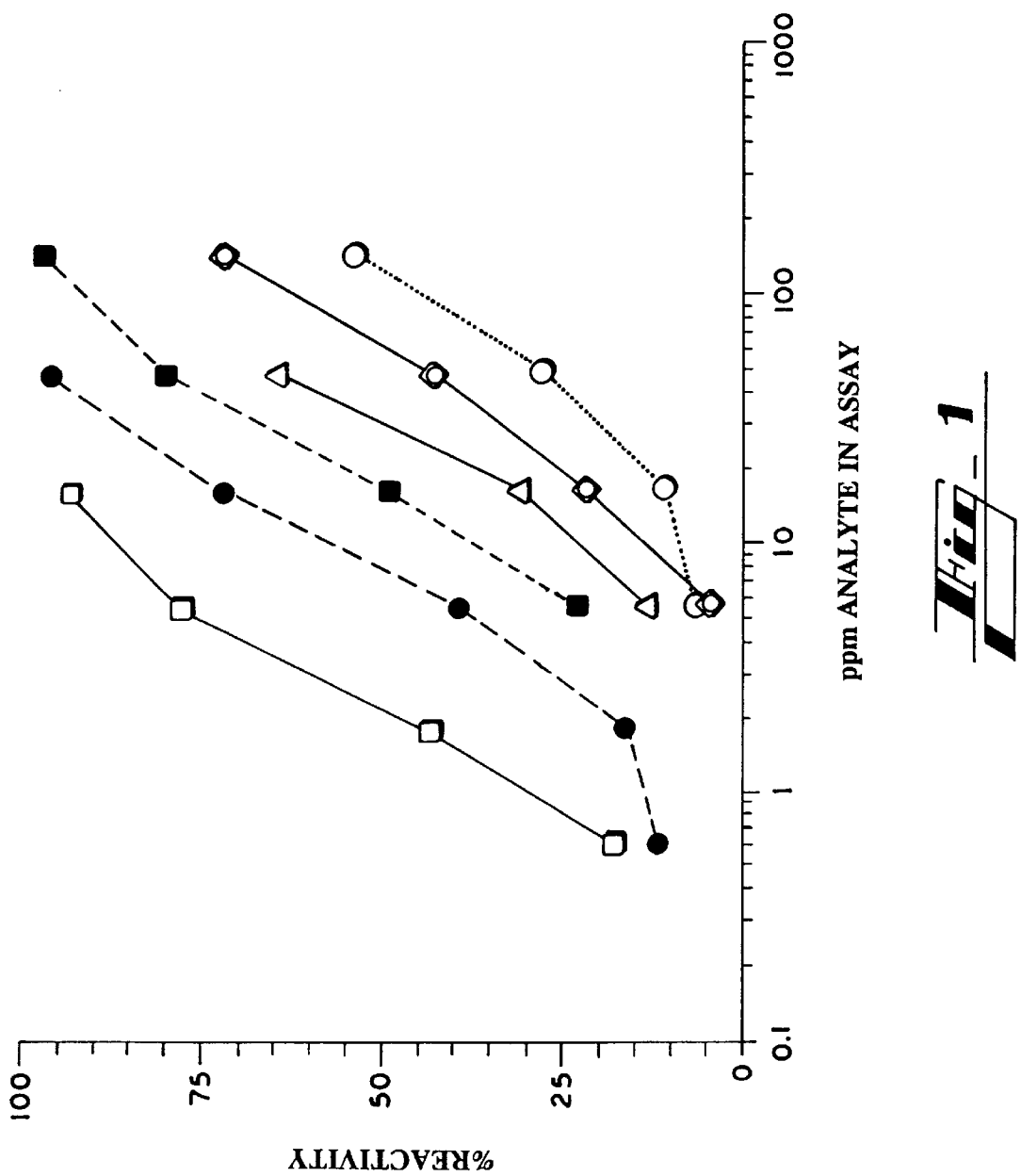
FIG. 1 is a graph showing percent reactivity of antibody with various concentrations of trichloroethylene, perchloroethylene, dichloroethenes, benzene, toluene, ethyl benzene and xylene (BTEX) using the reagents and a competitive immunoassay method as described herein. The open square symbol represents perchloroethylene, the closed circle symbol represents trichloroethylene, the open diamond symbol represents cis-1,2 dichloroethene, the open circle symbol represents trans-1,2 dichloroethene, the open triangle symbol represents 1,1 dichloroethene, and the closed square symbol represents BTEX.

Reagents, immunoassay methods, and kits for the detection of the analytes trichloroethylene and perchloroethylene in a sample are described herein. The reagents are immunogens, monoclonal or polyclonal antibodies prepared by immunizing an animal with the immunogens, and assay conjugates. The immunogens and assay conjugates are haptens structurally similar to trichloroethylene and perchloroethylene conjugated to a carrier through a linker group and a spacer group. Preferably, the structure comprising the hapten, linker and spacer groups of the immunogen used to produce the antibody is slightly different from the hapten, linker and spacer groups of the assay conjugate. The assay conjugates compete with the analytes for the antibodies. The antibodies are specific for the analytes trichloroethylene and perchloroethylene and exhibit minimal crossreactivity with other halogenated hydrocarbon compounds such as dichloroethylene and aromatic hydrocarbons such as benzene, toluene, ethyl benzene and xylene (commonly referred to by those skilled in the art as BTEX). Immunoassays employing these reagents are capable of detecting low concentrations of trichloroethylene and perchloroethylene in water and in soil. Kits containing these reagents provide for rapid analyte detection in the field.

The sensitivity and specificity of the antibody is dependent on the chemical structure of the immunogen used to elicit antibody production. Similarly, the sensitivity and specificity of the resulting immunoassay is dependent on the molecular interaction of the antibody with the assay conjugate. In general, the most desirable derivative for use in preparing an immunogen is one that is as structurally similar to the hapten as possible. However, with very small haptens such as trichloroethylene, the antibodies elicited by the immunogen often recognize and bind to atoms within the linking and spacer groups, which attach hapten to carrier, as well as to atoms comprising the hapten. Antibodies to very small haptens like trichloroethylene are typically of low affinity which ultimately limits immunoassay sensitivity. The affinity of these antibodies is higher to assay conjugates containing the same hapten, linking and spacer groups as the immunogen than to unmodified hapten. In order to provide for the most sensitive immunoassay, it is desirable to minimize binding to the assay conjugate while maximizing binding to free hapten in the sample. By careful selection of the atoms comprising the hapten, linking and spacer groups of the immunogen and assay conjugate, it is possible to manipulate sensitivity and specificity of the immunoassay.

Immunogens

Immunogens useful for producing antibodies to trichloroethylene and perchloroethylene contain a hapten, structurally similar to trichloroethylene or perchloroethylene, conjugated to an immunogenic carrier. The hapten contains two carbon atoms joined by a double bond with two chlorine atoms attached to one of the carbon atoms. The second carbon atom is bound to a chlorine or hydrogen atom and a linker group (Y). The linker group is attached to a spacer group (Z), which, in turn, is attached to the immunogenic carrier (W). The chemical formula of the immunogen is set forth below.

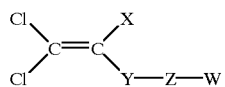

wherein X is Cl or H; Y is $CH_2$, NH, O or S; Z is 0–50 atoms arranged in a straight or branched chain or rings through saturated or unsaturated bonds; and W is an immunogenic carrier.

In a preferred immunogen, Y is $CH_2$ and Z is a straight chain containing oxygen and carbon atoms.

In a more preferred immunogen, X is Cl or H; Y is $CH_2$; Z is 1–9 oxygen and carbon atoms arranged in a straight chain through saturated bonds; and W is an immunogenic carrier.

The most preferred embodiment of the immunogen has the following chemical formula:

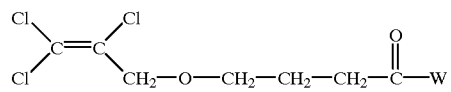

wherein W is an immunogenic carrier.

The most desirable derivative to use in preparing an immunogen has a structure as similar to the hapten as possible. The inclusion of a chlorine atom (Cl) in hapten group X provides for three chlorine atoms attached to the two double-bonded carbons of the hapten, thus closely mimicking the structure of trichloroethylene. Surprisingly, the substitution of a hydrogen atom (H) for chlorine in hapten group X also elicits the production of high affinity antibodies to trichloroethylene.

It has been unexpectedly discovered that when the linker group (Y) is $CH_2$, NH, O or S and the spacer group (Z) is a simple, linear, aliphatic chain, the immunogen causes the production of highly specific antibodies that have the greatest sensitivity to trichloroethylene and perchloroethylene and minimal crossreactivity with other halogenated and aromatic hydrocarbons.

The immunogenic carrier (W) is a large molecule, such as a protein, having the ability to provoke an immune response when administered to an animal. Suitable immunogenic carriers include proteins, polypeptides or peptides such as albumin, hemocyanin, thyroglobulin and derivatives thereof, particularly bovine serum albumin (BSA) and keyhole limpet hemocyanin (KLH), polysaccharides, carbohydrates, polymers, and solid phases. Other protein derived or non-protein derived substances are known to those skilled in the art. An immunogenic carrier typically has a molecular weight of at least 1,000 daltons, preferably greater than 10,000 daltons. Carrier molecules often contain a reactive group to facilitate covalent conjugation to the hapten. The carboxylic acid group or amine group of amino acids or the sugar groups of glycoproteins are often used in this manner. Carriers lacking such groups can often be reacted with an appropriate chemical to produce them. Preferably, an immune response is produced when the immunogen is injected into animals such as mice, rabbits, rats, goats, sheep, guinea pigs, chickens, and other animals, most preferably mice and rabbits.

Antibodies

Immunogens having the characteristics set forth above are used for the production of both monoclonal or polyclonal antibodies reactive toward trichloroethylene and perchloroethylene. The antibody exhibits minimal reactivity with dichloroethylene (including (cis) 1,2-dichloroethylene; 1,1-dichloroethylene; and (trans)1,2-dichloroethylene), and BTEX (the four aromatic hydrocarbon contaminants most frequently found in gasoline: benzene, toluene, ethylbenzene and xylene). The preferred antibody is a monoclonal antibody, due to its higher specificity for analyte.

Monoclonal antibodies are generated by methods well known to those skilled in the art. The preferred method is a modified version of the method of Kearney, et al., *J. Immunol.* 123:1548–1550 (1979), which is incorporated by reference herein. Briefly, animals such as mice or rabbits are inoculated with the immunogen in adjuvant, and spleen cells are harvested and mixed with a myeloma cell line, such as P3X63Ag8,653. The cells are induced to fuse by the addition of polyethylene glycol. Hybridomas are chemically selected by plating the cells in a selection medium containing hypoxanthine, aminopterin and thymidine (HAT). Hybridomas are subsequently screened for the ability to produce anti-trichloroethylene monoclonal antibodies. Hybridomas producing antibodies are cloned, expanded and stored frozen for future production.

The antibody may be labeled directly with a detectable label for identification and quantitation of trichloroethylene and perchloroethylene. Labels for use in immunoassays are generally known to those skilled in the art and include enzymes, radioisotopes, and fluorescent, luminescent and chromogenic substances including colored particles such as colloidal gold and latex beads.

Alternatively, the antibody may be labeled indirectly by reaction with labeled substances that have an affinity for immunoglobulin, such as protein A or G or second antibodies. The antibody may be conjugated with a second substance and detected with a labeled third substance having an affinity for the second substance conjugated to the antibody. For example, the antibody may be conjugated to biotin and the antibody-biotin conjugate detected using labeled avidin or streptavidin. Similarly, the antibody may be conjugated to a hapten and the antibody-hapten conjugate detected using labeled anti-hapten antibody. These and other methods of labeling antibodies and assay conjugates are well known to those skilled in the art.

Assay Conjugates

Assay conjugates reactive with the antibodies described above are useful in competitive immunoassays for trichloroethylene or perchloroethylene. The assay conjugate has a chemical formulation similar, but not identical, to that of the immunogen in that a hapten is bound to a chlorine or hydrogen atom (X) and a linker group (Y), which is attached to a spacer group (Z), which in turn is attached either directly by a chemical bond or indirectly through a linking molecule (W) to a detectable substance or solid phase, as shown in the following formula:

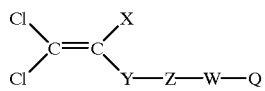

wherein X is Cl or H; Y is $CH_2$, NH, O or S; Z is 0–50 atoms arranged in a straight or branched chain or rings through saturated or unsaturated bonds; W is a chemical bond, protein, polysaccharide, peptide, polymer or other linking molecule; and Q is a detectable substance or solid phase. If W is a protein, it is a protein different from that utilized in the immunogen.

In a preferred assay conjugate, X is Cl; Y is $CH_2$; and Z is a straight chain containing nitrogen, oxygen and carbon atoms.

More preferably, X is Cl; Y is $CH_2$; Z is a straight chain containing nitrogen, oxygen and carbon atoms, including an aromatic ring; W is a protein; and Q is a detectable substance or solid phase.

In the most preferred embodiment, the assay conjugate has the following chemical structure:

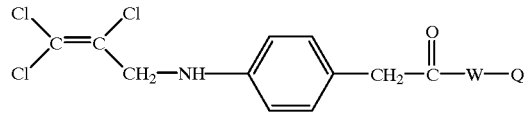

wherein W is a protein and Q is a solid phase.

The structure of the assay conjugate must be sufficiently similar to the immunogen used to elicit the antibody to provide for antibody binding. However, if the structure of the hapten, linking and spacer groups of the assay conjugate is identical to that of the immunogen, then the antibody will bind with greater affinity to the assay conjugate than to free hapten in the sample, thereby decreasing immunoassay sensitivity. Therefore, the structure of the assay conjugate must be similar enough to the immunogen to provide for antibody binding, but at the same time different enough so as to minimize binding of the antibody to the assay conjugate while maximizing binding to free hapten in the sample.

It has been unexpectedly discovered that antibodies elicited with immunogens having a chlorine atom as hapten group X can bind to, and be inhibited from binding to by free trichloroethylene, assay conjugates having a hydrogen atom as hapten group X. It has also been discovered that antibodies elicited with simple, linear, aliphatic linking and spacer groups Y and Z can bind to, and be inhibited from binding to by free trichloroethylene, assay conjugates having an aromatic ring in spacer group Z. These and other assay conjugate structures described above are contemplated herein.

The assay conjugate includes a physical means for separating bound from free detectable label or a detectable label (Q). When Q provides means for separating bound from free label, the hapten is attached through the linker and spacer groups to a solid phase substance. The terms "solid phase" and "solid phase substance" as used herein are defined to include non-liquid substances such as microtiter plates or plastic tube surfaces; particles, such as magnetic particles or latex beads; membranes; and other solid phases known to those skilled in the art. Preferred solid phases are those that are readily incorporated into rapid field screening kits. Exemplary solid phases include latex and magnetic particles and membranes, but may include any solid substance to which the hapten may be conjugated to allow antibody binding and separation of detectable label bound to the solid phase from unbound label.

Alternatively, the assay conjugate contains a detectable label (Q) including enzymes, radioisotopes and fluorescent, luminescent or chromogenic substances and other labels known to those skilled in the art.

Immunoassays

A highly sensitive trichloroethylene and perchloroethylene immunoassay employing antibodies, prepared from immunogens as described above, and assay conjugates is provided.

The immunoassay is useful for detecting the presence or amount of trichloroethylene and perchloroethylene in a variety of samples, particularly environmental samples such as contaminated soil or water. The sample may be obtained from any source in which the trichloroethylene and perchloroethylene are accessible to the antibody. For example, the sample may be a biological fluid, such as blood serum, blood plasma, urine, spinal fluid, fermentation fluid, lymph fluid, tissue culture fluid and ascites fluid; any plant tissue or extract including root, stem, leaf, or seed; industrial, agricultural or chemical effluent, process stream, reaction mixture or finished product; or an environmental material such as water, including water from oceans, lakes, rivers, streams, ponds, aquifers, and wetlands; soil; sediment; sludge; or air.

The antibody and assay conjugates may be employed in any heterogeneous or homogeneous, competitive immunoassay for the detection of trichloroethylene and perchloroethylene. Either the antibody or assay conjugate are labeled with a detectable label or coupled to a solid phase. Methods for coupling assay conjugates and antibodies to solid phases are well known to those skilled in the art. In accordance with the immunoassay method, the sample containing the hapten analyte, antibody, and assay conjugate are reacted together for a sufficient amount of time under conditions that promote the binding of antibody to trichloroethylene or perchloroethylene in the sample. It will be understood by those skilled in the art that the immunoassay reagents and sample may be reacted in different combinations and orders. A physical means is employed to separate reagents bound to the solid phase from unbound reagents such as filtration of particles, decantation of reaction solutions from coated tubes or wells, magnetic separation, capillary action, and other means known to those skilled in the art. It will also be understood that a separate washing of the solid phase may be included in the method. Either bound or free label can be quantitated as a measure of hapten analyte in the sample. When unbound label is quantitated, the signal from the immunoassay is directly proportional to concentration of hapten in the sample. When bound label is quantitated, the signal from the immunoassay is inversely proportional to hapten concentration.

Most preferably, the immunoassay is a dual particle immunoassay as described in U.S. patent application Ser. No. 08/623,614, entitled "Dual Particle Immunoassay Method and Kit", by Hajizadeh et al., filed Mar. 29, 1996, now abandoned, which is incorporated by reference herein. Briefly, in the dual particle competitive immunoassay, the sample to be analyzed, the antibody specific for trichloroethylene, and a particle coated with the trichloroethylene assay conjugate are reacted and applied to a porous membrane. All of the reagents except for the coated particle are able to pass through the porous membrane. Preferably, colored particles coated with a binding substance, such as protein A, that binds to the antibody, are reacted with coated particles retained on the membrane surface. The colored particles will pass through the membrane if not complexed with the trichloroethylene assay conjugate-coated particle. Colored particles bind to the antibodies that complex with the trichloroethylene assay conjugate-coated particles in the absence of trichloroethylene in the sample and are detected.

FIG. 1 shows the results of a dual particle competitive immunoassay performed using an antibody elicited by immunization of mice with the most preferred immunogen and the most preferred assay conjugate described herein in accordance with the protocol set forth in Examples 1, 2, and 3 of U.S. patent application Ser. No. 08/623,614 now abandoned except that the antibody is specific for trichloroethylene and perchloroethylene, the analyte-coated particle is coated with the trichloroethylene assay conjugate described herein, and the assay is used to detect trichloroethylene and perchloroethylene. As shown in FIG. 1, the immunoassay has the greatest sensitivity and specificity for trichloroethylene and perchloroethylene.

In an alternative preferred embodiment, the sample is combined with both an antibody bound to a solid phase, such as a latex particle, and an assay conjugate to which is conjugated a detectable molecule, preferably an enzyme such as alkaline phosphatase, horse radish peroxidase or beta-galactosidase. Preferably, the solid phase is coated with the antibody and the assay conjugate is conjugated to alkaline phosphatase. The trichloroethylene and perchloroethylene in the sample competes with the assay conjugate for binding sites on the antibody. Any binding sites not occupied by the trichloroethylene or perchloroethylene in the sample are filled by the assay conjugate. The antibody-coated solid phase is separated from the nonreacted components of the assay, such as by collection using a filtering device or centrifugation and is then combined with a reactant that reacts with the assay conjugate, such as an enzyme substrate, and is detected. For example, if the assay conjugate contains an enzyme, such as alkaline phosphatase, the presence of the enzyme, bound to the antibody, will catalyze the enzyme substrate to form a colored product. The amount of color produced is inversely proportional to the concentration of trichloroethylene and perchloroethylene in the sample, such that less blue color indicates more trichloroethylene and perchloroethylene are present in the sample.

The concentration of trichloroethylene and perchloroethylene in the sample is determined either by comparing the intensity of the color produced by the sample to a color card or by using a reflectometer.

The order in which the antibody, assay conjugate, and sample are combined can be altered to suit the particular parameters of the desired immunoassay. Preferably, the antibody, assay conjugate, and sample are combined and reacted together. Alternatively, for example, the antibody and sample are combined first and added as a mixture to the assay conjugate to optimize the binding of antibody to trichloroethylene and perchloroethylene in the sample, or the assay conjugate and sample are combined and the antibody added to that mixture.

The resulting reaction mixture, or combination of antibody, assay conjugate, and sample, is prepared in a solution that optimizes antibody-analyte binding kinetics. An appropriate solution is an aqueous solution or buffer. The solution is preferably provided under conditions that will promote specific binding, minimize nonspecific binding, solubilize analyte, stabilize and preserve reagent reactivity, and may contain buffers, detergents, solvents, salts, chelators, proteins, polymers, carbohydrates, sugars, and other substances known to those skilled in the art.

The reaction mixture solution is reacted for a sufficient amount of time to allow the antibody to react and bind to the analyte to form an antibody-analyte complex. The shortest amount of reaction time that results in binding is desired to minimize the time required to complete the assay. An appropriate reaction time period is less than or equal to one hour or between approximately one minute and one hour. A reaction time of less than fifteen minutes is preferred. Most preferably, the reaction time is less than three minutes. By optimizing the reagents, binding may be substantially completed as the reagents are combined.

The reaction is performed at any temperature at which the reagents do not degrade or become inactivated. A temperature between approximately 4° C. and 37° C. is preferred. The most preferred reaction temperature is ambient or room temperature (approximately 25° C.).

Immunoassay Kit

An immunoassay kit for the detection of trichloroethylene and perchloroethylene in a sample contains an assay conjugate and one or more antibodies prepared using the immunogens described above.

The kit may additionally contain equipment for safely obtaining the sample from the site of contamination, a vessel for containing the reagents, a timing means, a buffer for diluting the sample, and a colorimeter, reflectometer, or standard against which a color change may be measured. A simple, inexpensive reflectometer is preferred.

In a preferred embodiment, the reagents, including the antibody and assay conjugate are lyophilized, most preferably in a single vessel. Addition of aqueous sample to the vessel results in solubilization of the lyophilized reagents, causing them to react. Most preferably, the antibody and assay conjugate are sequentially lyophilized in a single container, in accordance with methods well known to those skilled in the art that minimize reaction by the reagents prior to addition of the sample.

The reagents, immunoassay methods, and kits described above will be further understood with reference to the following non-limiting examples.

EXAMPLE 1

Preparation of Immunogen for Production of Antibodies Specific for Trichloroethylene and Perchloroethylene An immunogen was prepared as follows for the subsequent production of monoclonal antibodies specific for trichloroethylene and perchloroethylene.

The hapten 4-(2,3,3-trichloro-2-propenyloxy)butyric, p-nitrophenyl ester was synthesized by known methods. The hapten (45 μL, 0.1 M) in dimethyformamide was added to 1 mL of a 10 mg/ml solution of keyhole limpet hemocyanin (KLH). The hapten (45 μL, 0.1 M) was also added to a 10 mg/ml solution of bovine serum albumin (BSA) in 0.1 M sodium bicarbonate, pH 8.5. The mixtures were reacted for three hours at room temperature with rocking to form hapten-protein conjugates. Unreacted hapten was removed by extensive dialysis against phosphate buffered saline (PBS).

Protein concentrations of the conjugates were determined by the bicinchoninic acid method (Pierce, Rockford, Ill.).

The conjugates were used to immunize mice and rabbits to elicit antibodies specific for trichloroethylene and perchloroethylene.

EXAMPLE 2

Preparation of Assay Conjugate for Use in Immunoassay for Detection of Trichloroethylene An assay conjugate was prepared as follows for subsequent use in a competitive immunoassay for the detection of trichloroethylene and perchloroethylene.

The hapten N-(2,3,3-trichloro-2-propenyl)-p-aminophenylacetic acid, p-nitrophenyl ester was synthesized by known methods. The hapten (45 μL, 0.1 M) in dimethyformamide was added to 1 mL of a 10 mg/ml solution of each of the following: ovalbumin, bovine serum albumin (BSA), and alkaline phosphatase) in 0.1 M sodium bicarbonate, pH 8.5. The mixtures were reacted for three hours at room temperature with rocking to form hapten-protein conjugates. Unreacted hapten was removed by extensive dialysis against phosphate buffered saline (PBS).

Protein concentrations of the conjugates were determined by the bicinchoninic acid method (Pierce, Rockford, Ill.).

The conjugates were used in competitive immunoassays in combination with antibodies for the detection of trichloroethylene and perchloroethylene.

Modifications and variations of the present reagents, methods and kits for detecting trichloroethylene and perchloroethylene will be obvious to those skilled in the art from the foregoing detailed description. Such modifications and variations are intended to come within the scope of the appended claims.

We claim:

1. An immunogen comprising a hapten bound to a linker group, which is bound to a spacer group, which is bound to an immunogenic carrier, wherein, when administered to an animal, the immunogen produces antibodies that bind to trichloroethylene and perchloroethylene, and are less than 25% reactive with halogenated or aromatic hydrocarbons other than trichloroethylene and perchloroethylene at concentrations less than 5 ppm, and wherein the immunogen has the following chemical formula:

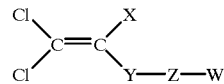

wherein $C_2Cl_2X$ is the hapten and X is Cl or H; Y is the linker group and is $CH_2$; Z is the spacer group and is 1–50 atoms arranged in a straight chain containing oxygen and carbon atoms; and W is the immunogenic carrier.

2. The immunogen of claim 1 wherein the carrier is selected from the group consisting of proteins, polypeptides, peptides, polysaccharides, carbohydrates, polymers, and solid phases.

3. An immunogen comprising a hapten bound to a linker group, which is bound to a spacer group, which is bound to an immunogenic carrier, wherein, when administered to an animal, the immunogen produces antibodies that bind to trichloroethylene and perchloroethylene, and are less than 25% reactive with halogenated or aromatic hydrocarbons other than trichloroethylene and perchloroethylene at concentrations less than 5 ppm, and wherein the immunogen has the following chemical formula:

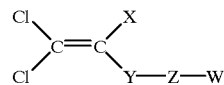

wherein $C_2Cl_2X$ is the hapten and X is Cl or H; Y is the linker group and is $CH_2$; Z is the spacer group and is 1–9 oxygen and carbon atoms arranged in a straight chain through saturated bonds; and W is the immunogenic carrier.

4. An immunogen comprising a hapten bound to a linker group, which is bound to a spacer group, which is bound to an immunogenic carrier, wherein, when administered to an animal, the immunogen produces antibodies that bind to trichloroethylene and perchloroethylene, and are less than 25% reactive with halogenated or aromatic hydrocarbons other than trichloroethylene and perchloroethylene at concentrations less than 5 ppm, and wherein the immunogen has the following chemical formula:

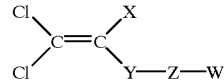

wherein $C_2Cl_2X$ is the hapten and X is Cl; Y is the linker group and is $CH_2$; Z is $C_4H_6O_2$ arranged in a straight chain; and W is the immunogenic carrier.

* * * * *